(12) United States Patent
Beaudet et al.

(10) Patent No.: US 8,242,083 B2
(45) Date of Patent: Aug. 14, 2012

(54) KINASE SUBSTRATES

(75) Inventors: Lucille Beaudet, Varennes (CA); Philippe Roby, Montreal (CA); Julie Blouin, LaSalle (CA)

(73) Assignee: PerkinElmer Health Sciences, Inc., Waltham, MA (US)

( * ) Notice: Subject to any disclaimer, the term of this patent is extended or adjusted under 35 U.S.C. 154(b) by 399 days.

(21) Appl. No.: 12/490,031

(22) Filed: Jun. 23, 2009

(65) Prior Publication Data

US 2010/0015650 A1   Jan. 21, 2010

Related U.S. Application Data

(60) Provisional application No. 61/074,969, filed on Jun. 23, 2008.

(51) Int. Cl.
*A61K 38/10* (2006.01)
*A61K 38/16* (2006.01)
*G01N 33/533* (2006.01)

(52) U.S. Cl. ......... 514/21.4; 530/326; 514/7.5; 436/546

(58) Field of Classification Search .................. None
See application file for complete search history.

(56) References Cited

U.S. PATENT DOCUMENTS

2004/0146961 A1 * 7/2004 Noland ..................... 435/21
2008/0003630 A1   1/2008 Notoya et al.

FOREIGN PATENT DOCUMENTS

WO   WO-00/61750     10/2000
WO   WO-2006/113050  * 10/2006

OTHER PUBLICATIONS

Budde, 1995, Biochimica et Biophysica Acta, 1248, 50-56.*
Blouin, J. et al., Novel Substrates for Fluorescence-based Protein Tyrosine Kinase Assays, GTC 3rd Kinases in Drug Discovery Conference, May 2008.
Brunati, A. et al., Phosphorylation of small peptides by spleen TPK-IIA, a tyrosine protein kinase stimulated by polylysine and by high ionic strength, *FEBS Letters*, 254(1,2): 145-9, Aug. 1989.
Budde, R. et al., Use of synthetic peptides and copolymers to study the substrate specificity and inhibition of the protein tyrosine kinase pp. $60^{c-src}$, *Biochimica et Blophysica Acta*, 1248: 50-56, 1995.
Donella-Deana, A. et al., Different specificities of spleen tyrosine protein kinases for synthetic peptide substrates, *European Journal of Biochemistry*, 194: 773-77, 1990.

* cited by examiner

*Primary Examiner* — Karlheinz R Skowronek
*Assistant Examiner* — Satyanarayana R Gudibande
(74) *Attorney, Agent, or Firm* — Gifford, Krass, Sprinkle, Anderson & Citkowski, P.C.

(57) ABSTRACT

Tyrosine kinase substrates are described herein that are phosphorylated by many and diverse tyrosine kinases, and are chemically stable relative to co-polymers of poly-EY or poly-EAY having random molecular weights in the range of 20-50 kDa. Tyrosine kinase substrate peptides are provided according to embodiments described herein which include an isolated tyrosine kinase substrate peptide having molecular weight in the range of about 0.5 kD-10 kD. Tyrosine kinase substrate peptides are provided according to embodiments described herein having no more than 50 amino acids. The peptides include 2-25 phosphorylation modules and each phosphorylation module has 2-3 amino acid residues.

15 Claims, 2 Drawing Sheets

SEQUENCE LISTING

<160> NUMBER OF SEQ ID NOS: 6

<210> SEQ ID NO 1
<211> LENGTH: 26
<212> TYPE: PRT
<213> ORGANISM: Artificial Sequence

```
<220> FEATURE:
<223> OTHER INFORMATION: tyrosine kinase substrate peptide

<400> SEQUENCE: 1

Ala Tyr Glu Ala Tyr Glu Ala Tyr Glu Lys Glu Tyr Ala Glu Tyr Ala
1               5                   10                  15

Glu Tyr Ala Lys Ala Tyr Ala Glu Tyr Glu
            20                  25

<210> SEQ ID NO 2
<211> LENGTH: 15
<212> TYPE: PRT
<213> ORGANISM: Artificial Sequence
<220> FEATURE:
<223> OTHER INFORMATION: tyrosine kinase substrate peptide

<400> SEQUENCE: 2

Ala Tyr Glu Ala Tyr Glu Ala Tyr Glu Ala Tyr Ala Glu Tyr Glu
1               5                   10                  15

<210> SEQ ID NO 3
<211> LENGTH: 28
<212> TYPE: PRT
<213> ORGANISM: Artificial Sequence
<220> FEATURE:
<223> OTHER INFORMATION: tyrosine kinase substrate peptide

<400> SEQUENCE: 3

Cys Ala Tyr Glu Ala Tyr Glu Ala Tyr Glu Lys Glu Tyr Ala Glu Tyr
1               5                   10                  15

Ala Glu Tyr Ala Lys Ala Tyr Ala Glu Tyr Glu Arg
            20                  25

<210> SEQ ID NO 4
<211> LENGTH: 22
<212> TYPE: PRT
<213> ORGANISM: Artificial Sequence
<220> FEATURE:
<223> OTHER INFORMATION: tyrosine kinase substrate peptide

<400> SEQUENCE: 4

Cys Gly Gly Glu Ala Tyr Glu Ala Tyr Glu Ala Tyr Glu Ala Tyr Ala
1               5                   10                  15

Glu Tyr Glu Ala Arg Arg
            20

<210> SEQ ID NO 5
<211> LENGTH: 26
<212> TYPE: PRT
<213> ORGANISM: Artificial Sequence
<220> FEATURE:
<223> OTHER INFORMATION: tyrosine kinase substrate peptide
<220> FEATURE:
<221> NAME/KEY: MISC_FEATURE
<222> LOCATION: (10)..(10)
<223> OTHER INFORMATION: "Xaa" has been inserted for "B" due to the
      technical requirements of Patent-In program.  As indicated in
      the specification, this symbol refers to a basic amino acid
      residue independently selected from histidine, lysine and
      arginine.
<220> FEATURE:
<221> NAME/KEY: MISC_FEATURE
<222> LOCATION: (20)..(20)
<223> OTHER INFORMATION: "Xaa" has been inserted for "B" due to the
      technical requirements of Patent-In program.  As indicated in
      the specification, this symbol refers to a basic amino acid
      residue independently selected from histidine, lysine and
      arginine.
```

```
<400> SEQUENCE: 5

Ala Tyr Glu Ala Tyr Glu Ala Tyr Glu Xaa Glu Tyr Ala Glu Tyr Ala
1               5                   10                  15

Glu Tyr Ala Xaa Ala Tyr Ala Glu Tyr Glu
            20                  25

<210> SEQ ID NO 6
<211> LENGTH: 4
<212> TYPE: PRT
<213> ORGANISM: Artificial Sequence
<220> FEATURE:
<223> OTHER INFORMATION: spacer module

<400> SEQUENCE: 6

Gly Ala Gly Ala
1
```

US 8,242,083 B2

KINASE SUBSTRATES

REFERENCE TO RELATED APPLICATION

This application claims priority from U.S. Patent Application Ser. No. 61/074,969, filed Jun. 23, 2008, the entire content of which is incorporated herein by reference.

FIELD OF THE INVENTION

The technology described herein relates to peptidic substrates for tyrosine kinase enzymes.

BACKGROUND OF THE INVENTION

Tyrosine kinases are a subgroup of the larger class of protein kinases and they function to transfer a phosphate group from ATP to a tyrosine residue in a protein. Phosphorylation of proteins by kinases is an important mechanism in signal transduction for regulating cell metabolism. Dysregulation of tyrosine kinase activity and expression is implicated in several diseases, which makes these enzymes valuable drug targets for the pharmaceutical industry. It is thus desirable to develop assays for the detection of their activity in cells and other biological systems and samples.

While most tyrosine kinases have known specific substrates, it is convenient for in vitro kinase assays to use a general purpose substrate that can be recognized by more than one tyrosine kinase. Poly-(Glu-Ala-Tyr), also known as poly-GAT or poly-EAY, and poly-(Glu, Tyr), also known as poly-GT or poly-EY, are heterogeneous co-polymer substrates that can be phosphorylated by a variety of tyrosine kinases.

Poly-(Glu-Ala-Tyr) is a copolymer made by the random polymerization of glutamic acid (E), alanine (A) and tyrosine (Y) in various molar ratios. Poly-(Glu-Ala-Tyr) is commercially available (e.g. Sigma-Aldrich Co.) as random copolymers 1:1:1 and 6:3:1 ratios. Poly-(Glu, Tyr) is a random co-polymer of glutamic acid and tyrosine, usually in a 4:1 ratio. Both types of polymer are heterogeneous in size, with molecular weights ranging from 20,000 to 50,000 Da.

The heterogeneity of these mixtures of random copolymers, poly-EY and poly-EAY, in many assay formats raises problems of variability in labeling with dyes, fluorophores or tag groups, and/or performance in kinase assays. In addition, these heterogeneous mixtures of random co-polymers have limited stability in solution. Once dissolved in aqueous buffer, both poly-EY and poly-EAY have to be kept, even for short term storage, at −80° C. to preserve their functionality as kinase substrates. Further, these heterogeneous mixtures of random co-polymers have limited stability in particular kinase assays, such as time-resolved fluorescence energy transfer (TR-FRET) kinase assays.

There is a continuing need for stable, homogeneous, generic peptide substrates phosphorylated by multiple tyrosine kinases.

SUMMARY OF THE INVENTION

Tyrosine kinase substrates are described herein that are phosphorylated by many and diverse tyrosine kinases, and are chemically stable relative to co-polymers of poly-EY or poly-EAY having random molecular weights in the range of 20-50 kDa.

Tyrosine kinase substrate peptides are provided according to embodiments described herein which include an isolated tyrosine kinase substrate peptide having molecular weight in the range of about 0.5 kD-10 kD. Tyrosine kinase substrate peptides are provided according to embodiments described herein having no more than 50 amino acids. The peptide includes 2-25 phosphorylation modules and each phosphorylation module has 2-3 amino acid residues.

In particular embodiments, each phosphorylation module has 2-3 amino acid residues, including at least one glutamic acid residue and at least one tyrosine residue in each phosphorylation module.

In further embodiments, the peptide includes 2-25 tripeptide phosphorylation modules, wherein each tripeptide phosphorylation module has at least a glutamic acid residue, a tyrosine residue, and an amino acid residue X, where X is any amino acid residue. For example, each X is independently an alanine residue or a glycine residue.

Optionally, one or more additional phosphorylation modules including tyrosine are included in a peptide substrate. Such additional phosphorylation modules include at least one tyrosine residue and two amino acid residues X, where each X can independently be any amino acid residue. Non-limiting examples of such additional phosphorylation modules include AYA and GYG.

Embodiments of tyrosine kinase substrate peptides are provided which include a peptide having the structural formula: $(Z_1)(E,Y,X_1)_n(Z_2)(X_2,Y,X_3)_m(Z_3)$, where n/n+m is 0.8 or greater; where m/n+m is 0.2 or less; where n+m is in the range of 2-25; where $X_1$ is any amino acid residue or is not present; where $X_2$ and $X_3$ are each independently any amino acid residue; where each of the n di- or tri-peptides is a phosphorylation module; where each of the m tri-peptides is a phosphorylation module; where E, Y, and $X_1$ are present in any order in each of the n phosphorylation modules; where $X_2$, Y, $X_3$ are present in any order in each of the m phosphorylation modules; where $Z_1$, $Z_2$ and $Z_3$ are each independently a nullity, any amino acid residue or a peptide having from 2-5 amino acids; where each substrate peptide having the structural formula: $(Z_1)(E,Y,X_1)_n(Z_2)(X_2,Y,X_3)_m(Z_3)$ has a molecular weight in the range of about 0.5 kD-10 kD.

Tyrosine kinase substrate peptides are provided according to embodiments of the present invention wherein the peptide includes at least one basic amino acid residue, exemplified by, but not limited to, histidine, lysine and arginine.

A tyrosine kinase substrate peptide is provided according to embodiments of the present invention wherein the peptide of the composition includes the amino acid sequence:

AYE AYE AYE K EYA EYA EYA K AYA EYE   (SEQ ID NO. 1)

A tyrosine kinase substrate peptide is provided according to embodiments of the present invention wherein the peptide of the composition includes the amino acid sequence: AYE AYE AYE B EYA EYA EYA B AYA EYE (SEQ ID NO. 5), where each "B" is a basic amino acid residue independently selected from histidine, lysine and arginine.

A tyrosine kinase substrate peptide is provided according to embodiments of the present invention wherein the peptide of the composition includes the amino acid sequence:

AYE AYE AYE AYA EYE.    (SEQ ID NO. 2)

Tyrosine kinase substrate compositions are provided according to embodiments of the present invention which include a plurality of isolated tyrosine kinase substrate peptides. Each peptide of the plurality of peptides in a composition has the same amino acid sequence and a molecular weight in the range of about 0.5 kD-10 kD. Each peptide of the plurality includes 2-25 phosphorylation modules and each phosphorylation module has 2-3 amino acid residues.

In particular embodiments, each phosphorylation module has 2-3 amino acid residues, including at least one glutamic acid residue and at least one tyrosine residue in each phosphorylation module.

In further embodiments, each peptide of the plurality includes 2-25 tripeptide phosphorylation modules, wherein each tripeptide phosphorylation module has at least a glutamic acid residue, a tyrosine residue, and an amino acid residue X, where X is any amino acid residue. For example, each X is independently an alanine residue or a glycine residue.

Embodiments of tyrosine kinase substrate compositions are provided which include peptides having the structural formula: $(Z_1)(E,Y,X_1)_n(Z_2)(X_2,Y,X_3)_m(Z_3)$, where n/n+m is 0.8 or greater; where m/n+m is 0.2 or less; where n+m is in the range of 2-25; where $X_1$ is any amino acid residue or is not present; where $X_2$ and $X_3$ are each independently any amino acid residue; where each of the n di- or tri-peptides is a phosphorylation module; where each of the m tri-peptides is a phosphorylation module; where E, Y, and $X_1$ are present in any order in each of the n phosphorylation modules; where $X_2$, Y, $X_3$ are present in any order in each of the m phosphorylation modules; where $Z_1$, $Z_2$ and $Z_3$ are each independently a nullity, any amino acid residue or a peptide having from 2-5 amino acids; where each substrate peptide having the structural formula: $(Z_1)(E,Y,X_1)_n(Z_2)(X_2,Y,X_3)_m(Z_3)$ has a molecular weight in the range of about 0.5 kD-10 kD and where all of the substrate peptides having the structural formula: $(Z_1)(E,Y,X_1)_n(Z_2)(X_2,Y,X_3)_m(Z_3)$ in the tyrosine kinase substrate composition have the same amino acid sequence.

Tyrosine kinase substrate compositions are provided according to embodiments of the present invention wherein each peptide of the plurality of peptides in the composition includes at least one basic amino acid residue, exemplified by, but not limited to, histidine, lysine and arginine.

A tyrosine kinase substrate composition is provided according to embodiments of the present invention wherein each peptide of the composition includes the amino acid sequence:

AYE AYE AYE K EYA EYA EYA K AYA EYE (SEQ ID NO. 1)

A tyrosine kinase substrate composition is provided according to embodiments of the present invention wherein each peptide of the composition includes the amino acid sequence: AYE AYE AYE B EYA EYA EYA B AYA EYE (SEQ ID NO. 5), where each "B" is a basic amino acid residue independently selected from histidine, lysine and arginine.

A tyrosine kinase substrate composition is provided according to embodiments of the present invention wherein each peptide of the composition includes the amino acid sequence:

AYE AYE AYE AYA EYE. (SEQ ID NO. 2)

Tyrosine kinase assays according to embodiments of the present invention include contacting a sample to be assayed for tyrosine kinase activity with a tyrosine kinase substrate composition as described herein and detecting phosphorylation of the tyrosine kinase substrates.

Kits for detection of kinase activity are provided according to embodiments which include a tyrosine kinase substrate composition as described herein. Optionally, instructions for use of the tyrosine kinase substrate composition in detecting kinase activity are included in an inventive kit.

DETAILED DESCRIPTION OF THE INVENTION

Figure 1:
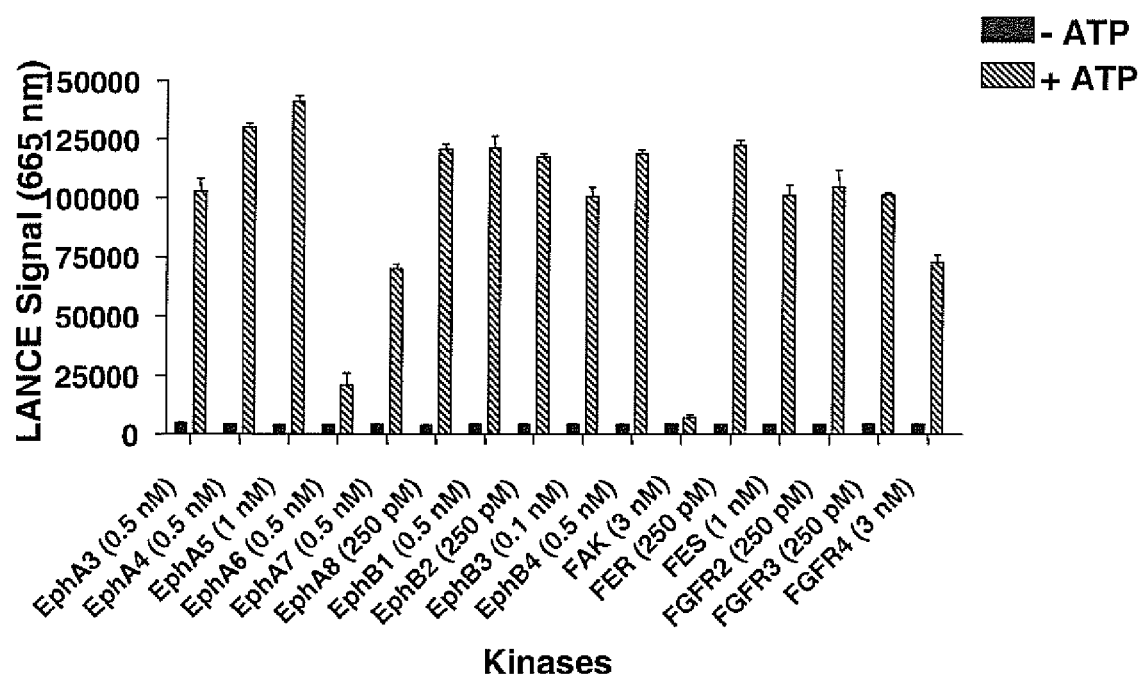
FIG. 1 is a graph showing tyrosine kinase assay data generated using a tyrosine kinase peptide substrate composition described herein.

The technology provided herein includes peptide substrates phosphorylated by multiple tyrosine kinases.

Peptides that serve as substrates for phosphorylation by multiple tyrosine kinases are provided according to embodiments of the present invention. In an embodiment, a peptide of the invention has a molecular weight in the range of about 0.5 kD-10 kD and includes 2-25 phosphorylation modules. Each phosphorylation module has 2-3 amino acid residues, including at least one glutamic acid residue and at least one tyrosine residue in each module. Exemplary phosphorylation modules include EY; YE; EYE; EYA; AYE; YEA; YAE; EAY and AEY.

In particular embodiments, peptide substrates for multiple tyrosine kinases are provided according to embodiments of the present invention which have a molecular weight in the range of about 1 kD-5 kD and include 2-25 phosphorylation modules. In further particular embodiments, peptide substrates phosphorylated by multiple tyrosine kinases are provided according to embodiments of the present invention which have a molecular weight in the range of about 1.5 kD-4 kD and include 2-20 phosphorylation modules.

Optionally, each peptide substrate contains 2, 3, 4, 5, 6, 7, 8, 9, 10, 11, 12, 13, 14, 15, 16, 17, 18, 19 20, 21, 22, 23, 24 or 25 phosphorylation modules.

Tyrosine kinase substrate peptides are provided according to embodiments described herein having no more than 50 amino acids. In particular embodiments, tyrosine kinase substrate peptides described herein have about 6 to about 50 amino acids.

As described herein, amino acids can be added to either the N-terminus or C-terminus of the peptides or both the N-terminus and C-terminus of the peptides, for instance, to add a functional moiety, such as a detectable label, capture moiety or immobilizing sequence.

In particular embodiments, tyrosine kinase substrate peptides described herein have no more than 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids. In further embodiments, the tyrosine kinase substrate peptide has no more than 50 amino acids, such as no more than 28 amino acids, no more than 27 amino acids, no more than 26 amino acids, no more than 22 amino acids or no more than 15 amino acids.

In further embodiments, tyrosine kinase substrate peptides described herein have no more than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids, wherein the number of phosphorylation module amino acids contained in a tyrosine kinase substrate peptide is at least 50% of the total number of amino acids contained in the tyrosine kinase substrate peptide. In further embodiments, the tyrosine kinase substrate peptide has no more than 50 amino acids, such as no more than 28 amino acids, no more than 27 amino acids, no more than 26 amino acids, no more than 22 amino acids or no more than 15 amino acids, wherein the number of phosphorylation module amino acids contained in a tyrosine kinase substrate peptide is at least 50% of the total number of amino acids contained in the tyrosine kinase substrate peptide.

In further embodiments, tyrosine kinase substrate peptides described herein have no more than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids, wherein the number of phosphorylation module amino acids contained in a tyrosine kinase substrate peptide is at least 70% of the total number of amino acids contained in the tyrosine kinase substrate peptide. In further embodiments, the tyrosine kinase substrate peptide has no more than 50 amino acids, such as no more than 28 amino acids, no more than 27 amino acids, no more than 26 amino acids, no more than 22 amino acids or no more than 15 amino acids, wherein the number of phosphorylation module amino acids contained in a tyrosine kinase substrate peptide is at least 70% of the total number of amino acids contained in the tyrosine kinase substrate peptide.

In further embodiments, each peptide substrate includes 2-25 tripeptide phosphorylation modules, wherein each tripeptide phosphorylation module has at least a glutamic acid residue, a tyrosine residue, and an amino acid residue X, where each X can independently be any amino acid residue. Optionally, each X is independently an alanine residue, a glutamic acid residue, or a glycine residue. For example, tripeptide phosphorylation modules including at least a glutamic acid residue (E), a tyrosine residue (Y), and an amino acid residue X where each X is independently an alanine residue (A), a glutamic acid residue (E) or alanine (A) include: EYE; EYA; AYE; YEA; YAE; EAY; AEY; EYG; GYE; EYE; YEG; YGE; EGY and GEY.

Optionally, one or more additional phosphorylation modules including tyrosine are included in a peptide substrate. Such additional phosphorylation modules include at least one tyrosine residue and two amino acid residues X, where each X can independently be any amino acid residue. Non-limiting examples of such additional phosphorylation modules include AYA and GYG.

Phosphorylation modules can be adjacent or separated by other amino acids, such as amino acids that function to alter or improve peptide solubility or stability, or which function as spacers between phosphorylation sites.

In some embodiments, one or more positively charged amino acid residues are present in the peptide sequence of the tyrosine kinase substrate peptides to facilitate solubility and purification at acidic pH. Thus, tyrosine kinase substrate peptides are provided according to embodiments of the present invention wherein each peptide includes at least one basic amino acid residue, exemplified by, but not limited to, histidine, lysine and arginine. The one or more positively charged amino acid residues are positioned at any location(s) in the tyrosine kinase substrate peptides. The one or more positively charged amino acid residues are positioned between phosphorylation modules in some embodiments. In further embodiments, the one or more positively charged amino acid residues are positioned at the N-terminus of the peptide and/or between the phosphorylation module closest to the N-terminus and the N-terminal amino acid residue. In further embodiments, the one or more positively charged amino acid residues are positioned at the C-terminus of the peptide and/or between the phosphorylation module closest to the C-terminus and the C-terminal amino acid residue.

In further embodiments, tyrosine kinase substrate peptides include at least one basic amino acid residue per ten amino acid residues. Thus, for example, a ten amino acid tyrosine kinase substrate peptide includes at least one basic amino acid residue according to embodiments of tyrosine kinase substrate peptides described herein. In a further example, a twenty amino acid tyrosine kinase substrate peptide includes at least two basic amino acid residues according to embodiments of tyrosine kinase substrate peptides described herein.

Any type of spacer is optionally included in a substrate peptide, for instance, to reduce or prevent interference of a label with phosphorylation of a substrate peptide. For example, a spacer can be a homo-bifunctional linker or a hetero-bifunctional linker linking the substrate peptide and label. depending on the identity of the moieties to be conjugated. In general, a spacer has about 1-20 backbone carbon atoms though a spacer may be larger or smaller depending on the identity of the substrate peptide and label. A spacer can be a natural or synthetic oligomer or polymer in some embodiments, such as agarose, carboxymethylcellulose, cellulose, dextran, polyaminopolystyrene, polyacrylamide, polyethylene or polyethylene glycol.

In some embodiments, one or more spacer amino acid residues are present in the peptide sequence of the tyrosine kinase substrate peptides. A spacer amino acid residue can be any amino acid residue. The one or more spacer amino acid residues are positioned at any location(s) in the tyrosine kinase substrate peptides. The one or more spacer amino acid residues are positioned between phosphorylation modules in some embodiments. In further embodiments, the one or more spacer amino acid residues are positioned at the N-terminus of the peptide and/or between the phosphorylation module closest to the N-terminus and the N-terminal amino acid residue. In further embodiments, the one or more spacer amino acid residues are positioned at the C-terminus of the peptide and/or between the phosphorylation module closest to the C-terminus and the C-terminal amino acid residue.

In certain embodiments, 1-5 spacer amino acid residues, 2-4 spacer amino acid residues or 3-4 spacer amino acid residues, are positioned at the N-terminus of the peptide and/or between the phosphorylation module closest to the N-terminus and the N-terminal amino acid residue where the tyrosine kinase substrate peptides are labeled at or near the N-terminus, in order to reduce any interference of the label with phosphorylation of the substrates.

In further embodiments, 1-5 spacer amino acid residues, 2-4 spacer amino acid residues or 3-4 spacer amino acid residues, are positioned at the N-terminus of the peptide and/or between the phosphorylation module closest to the N-terminus and the N-terminal amino acid residue where the tyrosine kinase substrate peptides are labeled at or near the N-terminus, in order to reduce any interference of the label with phosphorylation of the substrates.

Exemplary spacer amino acid residues include glycine and alanine, such as a GAGA (SEQ ID NO: 6) spacer module Embodiments of tyrosine kinase substrate peptides are provided which include peptides having the structural formula: $(Z_1)(E,Y,X_1)_n(Z_2)(X_2,Y,X_3)_m(Z_3)$, where n/n+m is 0.8 or greater; where m/n+m is 0.2 or less; where n+m is in the range of 2-25; where $X_1$ is any amino acid residue or is not present; where $X_2$ and $X_3$ are each independently any amino acid residue; where each of the n di- or tri-peptides is a phosphorylation module; where each of the m tri-peptides is a phosphorylation module; where E, Y, and $X_1$ are present in any order in each of the n phosphorylation modules; where $X_2$, Y, $X_3$ are present in any order in each of the m phosphorylation modules; where $Z_1$, $Z_2$ and $Z_3$ are each independently a nullity, any amino acid residue or a peptide having from 2-5 amino acids; where each substrate peptide having the structural formula: $(Z_1)(E,Y,X_1)_n(Z_2)(X_2,Y,X_3)_m(Z_3)$ has a molecular weight in the range of about 0.5 kD-10 kD and where all of the substrate peptides having the structural formula: $(Z_1)(E,Y,X_1)_n(Z_2)(X_2,Y,X_3)_m(Z_3)$ in the tyrosine kinase substrate composition have the same amino acid sequence.

Some in vitro kinase assays, such as radioactive phosphate incorporation, can be performed with unlabeled substrate peptides. Most non-radioactive kinase assays, such as TR-FRET, require that the substrate peptides are detectably labeled. Therefore, substrate peptides can be used in unlabeled and labeled form, depending on the selected assay format.

Substrate peptides can be labeled using any detectable label. The term "detectable label" refers to a substance that can be measured and/or observed, visually or by any appropriate method illustratively including spectroscopic, optical, photochemical, biochemical, enzymatic, electrical and/or immunochemical methods of detection, to indicate presence of the label. Non-limiting examples of non-radioactive detectable labels that can be used in conjunction with compositions and methods described herein illustratively include a fluorescent moiety, a chemiluminescent moiety, a bioluminescent moiety, a magnetic particle, a member of a specific binding pair, and a chromophore. For example, peptides can be labeled with a dye, such as a fluorophore, a chromophore, or a member of a specific binding pair such as biotin. The term "member of a specific binding pair" refers to a substance that specifically recognizes and interacts with a second substance exemplified by specific binding pairs such as biotin-avidin, biotin-streptavidin, antibody-antigen, and target-aptamer. Non-limiting examples of detectable labels that can be used include fluorescent dyes such as fluorescein, fluorescein isothiocyanate, rhodamine, rhodamine isothiocyanate, Texas Red, cyanine dyes such as Cyanine 3 and Cyanine 5, and ALEXA dyes; chromophores such as horseradish peroxidase, alkaline phosphatase and digoxigenin; binding partners such as biotin and biotin derivatives.

Substrate peptides according to embodiments include a FRET acceptor as a detectable label. FRET is a process involving transfer of energy by a donor label to an acceptor label when the donor label and acceptor label are in proximity.

In embodiments of the present invention, substrate peptides are coupled to a fluorescence resonance energy transfer (FRET) donor or acceptor. In further embodiments, substrate peptides are coupled to a FRET acceptor.

Detectable labels operable in FRET techniques of the present invention include flurophores and luminescent compounds illustratively including those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2'disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcouluarin (Coumaran 151); cyanosine; DAPOXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl}amino)naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid and terbium chelate derivatives.

Examples of FRET donor/acceptor fluorophore pairs are described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005.

One of skill in the art can easily determine which of various fluorophores are to be used as FRET donor/acceptor fluorophore pairs in a particular application. Examples of FRET acceptors include, but are not limited to, tetramethylrhodamine, fluorescein, 4-(4'-dimethylaminophenylazo)benzoic acid (dabcyl), BODIPY FL, QSY 7, QSY 9, Cy5 and Alexa647.

In particular embodiments, peptide tyrosine kinase substrates are labeled with ULIGHT FRET acceptor.

Labeling of a peptide tyrosine kinase substrate described herein can be achieved by any of various methods known to the skilled artisan. For example, the $NH_2$-terminus of the peptide can be labeled directly with a molecule having a NHS ester reactive group.

A detectable label can be conjugated to a peptide directly or indirectly, such as through a linker. Broadly described, conjugation of the detectable label to a peptide includes reaction of a functional group of the detectable label or linker that selectively reacts with a peptide functional group such as a terminal amino group, a terminal carboxyl group or a functional group of an amino acid side chain.

Non-limiting examples of functional groups which react with sulfhydryl groups of cysteine-containing peptides include epoxide, haloacetyl, and maleimide. Non-limiting examples of functional groups which react with amino groups include N-hydroxysuccinimidyl esters, carbodiimides, aldehydes, ketones, glyoxals, imidoesters, isothiocyanates, sulfonyl chlorides and acyl azides. Non-limiting examples of functional groups which react with carboxylic acid groups include amines, hydrazides, carbodiimides, diazoalkanes, diazoacetyls and carbonyldiimidazole. Additional functional groups and exemplary conjugation reactions are known in the art as exemplified in G. T. Hermanson, Bioconjugate Techniques, 2nd Edition, Academic Press, 2008.

A detectable label can be incorporated during and/or after peptide synthesis. A detectable label can be inserted at any position in a peptide where it does not interfere with the recognition of the peptide substrate by the tyrosine kinase being assayed, or with the binding of anti-phospho-antibodies used for the detection of the phospho-tyrosine residues in antibody-based assays.

In particular embodiments, a peptide tyrosine kinase substrate described herein is labeled by reaction of a cysteine residue of the peptide tyrosine kinase substrate with a fluorescent dye or linker having a functional group, such as a maleimide group, that reacts with a cysteine to create a covalent link between the dye and the peptide. In such embodiments, at least one cysteine residue is included in the peptide tyrosine kinase substrate and may be positioned anywhere in the tyrosine kinase substrate peptides, such as between phosphorylation modules, at the N-terminus of the peptide, between the phosphorylation module closest to the N-terminus and the N-terminal amino acid residue, at the C-terminus of the peptide and/or between the phosphorylation module closest to the C-terminus and the C-terminal amino acid residue.

A detectably labeled tyrosine kinase substrate peptide is provided according to embodiments having the structural formula: $(Z_1)(E,Y,X_1)_n(Z_2)(X_2,Y,X_3)_m(Z_3)$, where n/n+m is 0.8 or greater; where m/n+m is 0.2 or less; where n+m is in the range of 2-25; where $X_1$ is any amino acid residue or is not present; where $X_2$ and $X_3$ are each independently any amino acid residue; where each of the n di- or tri-peptides is a phosphorylation module; where each of the m tri-peptides is a phosphorylation module; where E, Y, and $X_1$ are present in any order in each of the n phosphorylation modules; where $X_2$, Y, $X_3$ are present in any order in each of the m phosphorylation modules; where $Z_1$, $Z_2$ and $Z_3$ are each independently a nullity, any amino acid residue or a peptide having from 2-5 amino acids; where each substrate peptide having the structural formula: $(Z_1)(E,Y,X_1)_n(Z_2)(X_2,Y,X_3)_m(Z_3)$ has a molecular weight in the range of about 0.5 kD-10 kD.

A particular labeled tyrosine kinase substrate peptide provided according to embodiments of the present invention includes the amino acid sequence: AYE AYE AYE K EYA EYA EYA K AYA EYE (SEQ ID NO. 1).

A particular labeled tyrosine kinase substrate peptide provided according to embodiments of the present invention includes the amino acid sequence: AYE AYE AYE AYA EYE (SEQ ID NO.2).

A particular labeled tyrosine kinase substrate peptide provided according to embodiments of the present invention includes the amino acid sequence: C AYE AYE AYE K EYA EYA EYA K AYA EYE R (SEQ ID NO. 3).

A particular labeled tyrosine kinase substrate peptide provided according to embodiments of the present invention includes the amino acid sequence: CGG E AYE AYE AYE AYA EYE ARR (SEQ ID NO.4)

A particular labeled tyrosine kinase substrate peptide provided according to embodiments of the present invention includes the amino acid sequence: AYE AYE AYE B EYA EYA EYA B AYA EYE (SEQ ID NO. 5), where each B is a basic amino acid residue independently selected from histidine, lysine and arginine.

In particular examples described herein, tyrosine kinase peptide substrate compositions include a cysteine residue at the N-terminus of the peptides.

In particular embodiments, the number of phosphorylation module amino acids contained in a tyrosine kinase substrate peptide is at least 50% of the total number of amino acids contained in the tyrosine kinase substrate peptide. In further embodiments, the number of phosphorylation module amino acids contained in a tyrosine kinase substrate peptide is at least 70% of the total number of amino acids contained in the tyrosine kinase substrate peptide. In still further embodiments, the number of phosphorylation module amino acids contained in a tyrosine kinase substrate peptide is at least 80%, 81%, 82%, 83%, 84%, 85%, 86%, 87%, 88%, 89%, 90%, 91%, 92%, 93%, 94%, 95%, 96%, 97%, 98%, 99% or greater of the total number of amino acids contained in the tyrosine kinase substrate peptide.

As will be recognized by one of skill in the art, the N-terminus of peptides of the plurality of peptides in the composition may include either a free ($NH_2$) or acylated amine and the C-terminus may include free acid (COOH) or amidated ($CONH_2$) terminus. Additional or alternative modifications may be made, for instance, to facilitate peptide labeling.

A particular tyrosine kinase substrate peptide provided according to embodiments of the present invention includes the amino acid sequence: AYE AYE AYE K EYA EYA EYA K AYA EYE (SEQ ID NO. 1).

A tyrosine kinase substrate peptide is provided according to embodiments of the present invention wherein the peptide of the composition includes the amino acid sequence: AYE AYE AYE B EYA EYA EYA B AYA EYE (SEQ ID NO. 5), where each "B" is a basic amino acid residue independently selected from histidine, lysine and arginine.

A particular tyrosine kinase substrate peptide provided according to embodiments of the present invention includes the amino acid sequence: AYE AYE AYE AYA EYE (SEQ ID NO.2)

A particular tyrosine kinase substrate peptide provided according to embodiments of the present invention includes the amino acid sequence: C AYE AYE AYE K EYA EYA EYA K AYA EYE R (SEQ ID NO. 3);

Unlike random co-polymer tyrosine kinase substrates, the peptide tyrosine kinase substrates described herein are homogeneous, relatively simple to synthesize and show little variation from lot to lot. Once labeled, they can be stored for long periods of time at –20° C. and resist well freeze-thaw cycles.

Isolated tyrosine kinase substrate peptides are provided according to embodiments described herein. The peptide has a molecular weight in the range of about 0.5 kD-10 kD and includes 2-25 phosphorylation modules. Each phosphorylation module has 2-3 amino acid residues, including at least one glutamic acid residue and at least one tyrosine residue in each phosphorylation module.

In further embodiments, the peptide includes 2-25 tripeptide phosphorylation modules, wherein each tripeptide phosphorylation module has at least a glutamic acid residue, a tyrosine residue, and an amino acid residue X. Optionally, each X is independently an alanine residue or a glycine residue.

Tyrosine kinase substrate peptides are provided according to embodiments of the present invention wherein the peptide includes at least one basic amino acid residue, exemplified by, but not limited to, histidine, lysine and arginine.

A tyrosine kinase substrate peptide is provided according to embodiments of the present invention wherein the peptide includes the amino acid sequence: AYE AYE AYE K EYA EYA EYA K AYA EYE (SEQ ID NO. 1).

A tyrosine kinase substrate peptide is provided according to embodiments of the present invention wherein the peptide includes the amino acid sequence: AYE AYE AYE AYA EYE (SEQ ID NO.2)

Tyrosine kinase substrate compositions are provided according to embodiments which include a plurality of peptide substrates, wherein each peptide substrate has the same amino acid sequence and the same number of amino acids, thereby generating a homogeneous tyrosine kinase substrate composition.

Tyrosine kinase substrate compositions are provided according to embodiments which include a plurality of isolated tyrosine kinase substrate peptides. Each peptide of the plurality of peptides in a composition has the same amino acid sequence and a molecular weight in the range of about 0.5 kD-10 kD. Each peptide of the plurality includes 2-25 phosphorylation modules. Each phosphorylation module has 2-3 amino acid residues, including at least one glutamic acid residue and at least one tyrosine residue in each phosphorylation module.

In further embodiments, each peptide of the plurality includes 2-25 tripeptide phosphorylation modules, wherein each tripeptide phosphorylation module has at least a glutamic acid residue, a tyrosine residue, and an amino acid residue X. Optionally, each X is independently an alanine residue or a glycine residue.

Tyrosine kinase substrate compositions are provided according to embodiments of the present invention wherein each peptide of the plurality of peptides in the composition includes at least one basic amino acid residue, exemplified by, but not limited to, histidine, lysine and arginine.

A tyrosine kinase substrate composition is provided according to embodiments of the present invention wherein each peptide includes the amino acid sequence: AYE AYE AYE K EYA EYA EYA K AYA EYE (SEQ ID NO. 1).

A tyrosine kinase substrate composition is provided according to embodiments of the present invention wherein each peptide includes the amino acid sequence: AYE AYE AYA AYA EYE (SEQ ID NO.2)

Tyrosine kinase substrate compositions can include various amounts of a particular tyrosine kinase substrate peptide depending on the intended use. In general, tyrosine kinase substrate compositions include a particular tyrosine kinase substrate peptide in concentrations in the range of about 1 nM-1M, but can include greater or lesser concentrations.

Tyrosine kinase substrate compositions can include two or more isolated peptides as described herein. Such combinations of isolated peptides can be used, for example, to assay a broad range of kinases.

The terms "amino acid" and "amino acid residue" are well-known in the art. In general the abbreviations used herein for designating the amino acids and protective groups conform to those used by the IUPAC-IUB Commission on Biochemical Nomenclature, see for example Biochemistry (1972) 11:1726-1732. The following abbreviations are commonly used to refer to specific amino acids and/or amino acid residues: A or Ala for alanine, C or Cys for cysteine, D or Asp for aspartic acid, E or Glu for glutamic acid, F or Phe for phenylalanine, G or Gly for glycine, H or His for histidine, I or Ile for isoleucine, K or Lys for lysine, L or Leu for leucine, M or Met for methionine, N or Asn for asparagine, P or Pro for proline, Q or Gln for glutamine, R or Arg for arginine, S or Ser for serine, T or Thr for threonine, V or Val for valine, W or Trp for tryptophan, and Y or Tyr for tyrosine.

The term "amino acid residue" further includes analogs, derivatives and congeners of amino acids, as well as C-terminal or N-terminal protected amino acid derivatives. For example, an amino acid analog may be used wherein a side chain is modified while still providing a carboxyl, amino or other reactive functional group. For example, amino acid analogs illustratively include canavanine, cyanoalanine, diaminobutyric acid, diaminopimelic acid, dihydroxy-phenylalanine norleucine, 3-phosphoserine, homoserine, 5-hydroxytryptophan, 1-methylhistidine, 3-methylhistidine, and ornithine. Well-known modified amino acids and cyclic amino acids can be included in embodiments of tyrosine kinase substrate peptides.

Tyrosine kinase substrate peptides can be generated using well-known chemical methods of direct peptide synthesis, such as manual or automated solid-phase peptide synthesis, for example as described in P. Lloyd-Williams et al., Chemical Approaches to the Synthesis of Peptides and Proteins, CRC-Press, 1997; and M. W. Pennington et al., Peptide Synthesis Protocols, Humana Press, 1994. In addition, tyrosine kinase substrate peptides can be generated using well-known recombinant methodology for producing peptides, for example J. Sambrook and D. W. Russell, Molecular Cloning. A Laboratory Manual, Cold Spring Harbor Laboratory Press; 3rd Ed., 2001; F. M. Ausubel, Ed., Short Protocols in Molecular Biology, Current Protocols; 5th Ed., 2002; and Herdewijn, P. (Ed.), Oligonucleotide Synthesis: Methods and Applications, Methods in Molecular Biology, Humana Press, 2004.

The terms "isolated peptide" and "isolated peptides" refer to peptides which are substantially free of material such as chemical precursors or other chemicals used in peptide synthesis or substantially free of cellular material such as contaminating polypeptides when produced recombinantly.

Tyrosine kinase assays according to embodiments of the present invention include contacting a sample to be assayed for tyrosine kinase activity with a tyrosine kinase substrate composition as described herein and detecting phosphorylation of the tyrosine kinase substrates. Any tyrosine kinase assay format can be used in conjunction with tyrosine kinase substrate peptides and compositions described herein, including, but not limited to, immunoblotting, gel electrophoresis of labeled substrates, filter binding, immunoprecipitation, scintillation proximity assay, time-resolved fluorescence resonance energy transfer (TR-FRET), and fluorescence polarization assays.

Kits for detection of kinase activity are provided according to embodiments which include a tyrosine kinase substrate composition as described herein. Optionally, instructions for use of the tyrosine kinase substrate composition in detecting kinase activity are included in an inventive kit. Additional exemplary components of a kit for detection of kinase activity include a buffer, a control kinase, a control peptide, a detectable label and the like.

In particular embodiments, a kit for detection of kinase activity includes a tyrosine kinase substrate peptide having the structural formula: $(Z_1)(E,Y,X_1)_n(Z_2)(X_2,Y,X_3)_m(Z_3)$, where $n/n+m$ is 0.8 or greater; where $m/n+m$ is 0.2 or less; where $n+m$ is in the range of 2-25; where $X_1$ is any amino acid residue or is not present; where $X_2$ and $X_3$ are each independently any amino acid residue; where each of the n di- or tri-peptides is a phosphorylation module; where each of the m tri-peptides is a phosphorylation module; where E, Y, and $X_1$ are present in any order in each of the n phosphorylation modules; where $X_2$, Y, $X_3$ are present in any order in each of the m phosphorylation modules; where $Z_1$, $Z_2$ and $Z_3$ are each independently a nullity, any amino acid residue or a peptide having from 2-5 amino acids; where each substrate peptide having the structural formula: $(Z_1)(E,Y,X_1)_n(Z_2)(X_2,Y,X_3)_m(Z_3)$ has a molecular weight in the range of about 0.5 kD-10 kD.

In particular embodiments, a kit for detection of kinase activity includes a tyrosine kinase substrate peptide includes a tyrosine kinase substrate peptide including the amino acid sequence: AYE AYE AYE K EYA EYA EYA K AYA EYE (SEQ ID NO. 1).

In particular embodiments, a kit for detection of kinase activity includes a tyrosine kinase substrate peptide includes a tyrosine kinase substrate peptide including the amino acid sequence: AYE AYE AYE AYA EYE (SEQ ID NO.2).

In particular embodiments, a kit for detection of kinase activity includes a tyrosine kinase substrate peptide includes a tyrosine kinase substrate peptide including the amino acid sequence: C AYE AYE AYE K EYA EYA EYA K AYA EYE R (SEQ ID NO. 3).

In particular embodiments, a kit for detection of kinase activity includes a tyrosine kinase substrate peptide includes a tyrosine kinase substrate peptide including the amino acid sequence: CGG E AYE AYE AYE AYA EYE ARR (SEQ ID NO.4)

In particular embodiments, a kit for detection of kinase activity includes a tyrosine kinase substrate peptide includes a tyrosine kinase substrate peptide including the amino acid sequence: AYE AYE AYE B EYA EYA EYA B AYA EYE (SEQ ID NO. 5), where each B is a basic amino acid residue independently selected from histidine, lysine and arginine.

Embodiments of inventive compositions and methods are illustrated in the following examples. These examples are provided for illustrative purposes and are not considered limitations on the scope of inventive compositions and methods.

Example 1

The peptide of SEQ ID No. 1 is modified for labeling by addition of an N-terminal cysteine and by addition of a C-terminal basic amino acid to increase solubility at low pH. The resulting exemplary tyrosine kinase substrate peptide, termed BRB1: C AYE AYE AYE K EYA EYA EYA K AYA EYE R (SEQ ID NO:3), is generated using well-known methods of peptide chemical synthesis. The BRB1 tyrosine kinase substrate peptide contains eight tyrosines, some of which are in the same module context (AYE and EAY) while other others are in a unique module context (AYA and EYE). The BRB1 tyrosine kinase substrate peptide includes three positively charged residues which improve solubility at lower pH.

TR-FRET kinase assays are performed under standardized conditions: various individual kinases are incubated with 50 nM of kinase substrate BRB1 labeled with the TR-FRET acceptor dye ULight (PerkinElmer) and 200 micromolar ATP in 10 µL of kinase assay buffer (50 mM HEPES pH7.5, 10 mM MgCl$_2$, 3 mM MnCl$_2$, 1 mM EGTA, 2 mM DTT and 0.01% Tween-20) for 2 hours at room temperature. Reactions are stopped with EDTA, and anti-phospho-tyrosine antibodies (clone PT66) labeled with the TR-FRET europium chelate donor dye are added to a final concentration of 2 nM in a final volume of 20 µL. The TR-FRET signal emitted at 665 nm is read one hour after the addition of antibodies using a TR-FRET plate reader such as the Envision® Multilabel Plate reader (PerkinElmer). The emitted signal at 665 nm is proportional to the extent of peptide phosphorylation, Control reactions indicative of background are performed excluding ATP from the reaction.

FIG. 1 shows data generated in graphic form and indicates amounts of each kinase included in the reactions.

Example 2

To demonstrate further its function as a generic tyrosine kinase substrate, the dye-labeled peptide of SEQ ID No. 3 is used in 83 TR-FRET kinase assays with the europium-labeled-anti-phospho-tyrosine antibody PT66. Assay conditions are identical to those used described for FIG. 1.

Tables I and II show that 72 kinases tested out of 83 (87%) phosphorylated peptide of sequence ID No. 3, with a signal to noise ratio of >3.

TABLE I

| Cytoplasmic Tyrosine Kinases | | |
|---|---|---|
| Kinase | Kinase Concentration (nM) | Signal to Noise Ratio with BRB1 Peptide |
| ABL | 0.25 | 4.1 |
| ABL [T315I] (ABL1) | 0.5 | 4.8 |
| ACK | 20 | 17.3 |
| ARG | 0.5 | 10.6 |
| BLK | 0.5 | 31.0 |
| BMX | 0.5 | 7.1 |
| BRK | 3 | 2.4 |
| BTK | 0.25 | 6.8 |
| CSK | 20 | 27.2 |
| CTK | 20 | 2.5 |
| FAK | 3 | 1.7 |
| FER | 0.25 | 31.0 |
| FES | 1 | 24.9 |
| FGR | 0.1 | 29.3 |
| FRK | 0.5 | 9.7 |
| FYN | 0.25 | 25.9 |
| HCK | 0.25 | 29.7 |
| ITK | 0.5 | 8.4 |
| JAK1 | 7 | 13.7 |
| JAK2 | 1 | 35.5 |
| JAK3 | 0.5 | 16.1 |
| LCK | 0.5 | 12.3 |
| LYNa | 0.5 | 32.5 |
| LYNb | 1 | 33.1 |
| PYK2 | 0.25 | 2.9 |
| SRC | 0.5 | 31.7 |
| SRM | 0.5 | 32.5 |
| SYK | 0.5 | 24.6 |
| TEC | 0.5 | 18.6 |
| *TNK1* | 1 | 6.8 |
| TXK | 3 | 5.9 |
| TYK2 | 4 | 7.3 |
| YES | 0.25 | 28.0 |
| ZAP70 | 4 | 7.6 |

TABLE II

| Receptor Tyrosine Kinases | | |
|---|---|---|
| Kinase | Kinase Concentration (nM) | Signal to Noise ratio with BRB1 Peptide |
| ALK | 4 | 8.8 |
| AXL | 4 | 1.8 |
| DDR1 | 0.5 | 1.0 |
| DDR2 | 0.5 | 1.0 |
| EGFR | 0.5 | 10.0 |
| DGFR [T790M] | 0.5 | 3.3 |
| EphA1 | 0.5 | 10.8 |
| EphA2 | 0.25 | 26.9 |
| EphA3 | 0.5 | 22.4 |
| EphA4 | 0.5 | 31.5 |
| EphA5 | 1 | 35.5 |
| EphA6 | 0.5 | 5.4 |
| EphA7 | 0.5 | 17.2 |
| EphA8 | 0.25 | 32.3 |
| EphB1 | 0.5 | 29.9 |
| EphB2 | 0.25 | 28.8 |
| EphB3 | 0.1 | 24.7 |
| EphB4 | 0.5 | 29.8 |
| FGFR1 | 0.5 | 26.4 |
| FGFR2 | 0.25 | 27.1 |

TABLE II-continued

Receptor Tyrosine Kinases

| Kinase | Kinase Concentration (nM) | Signal to Noise ratio with BRB1 Peptide |
|---|---|---|
| FGFR3 | 0.25 | 24.4 |
| FGFR4 | 3 | 17.7 |
| FLT1 | 0.25 | 4.1 |
| FLT3 | 0.1 | 25.9 |
| FLT4 | 0.25 | 20.0 |
| FMS (CSFR) | 0.25 | 3.0 |
| HER2 | 10 | 1.4 |
| HER4 (ERBB4) | 0.1 | 3.1 |
| IGF1R | 0.25 | 25.1 |
| INSR | 20 | 4.0 |
| IRR | 0.5 | 19.2 |
| KDR | 0.25 | 16.9 |
| KIT | 2 | 1.5 |
| LTK | 1 | 13.7 |
| MER | 0.25 | 12.9 |
| MET | 0.5 | 24.2 |
| MUSK | 1 | 3.1 |
| PDGFRa | 0.5 | 8.0 |
| PDGFRβ | 0.25 | 4.7 |
| RET | 0.5 | 20.3 |
| RON | 0.25 | 3.5 |
| ROR1 | 20 | 1.1 |
| ROR2 | 20 | 1.0 |
| ROS | 0.25 | 24.5 |
| TIE2 | 0.5 | 17.7 |
| TRKA (NTRK1) | 0.5 | 23.2 |
| TRKB (NTRK2) | 0.5 | 28.0 |
| TRKC (NTRK3) | 0.5 | 6.4 |
| TYRO3 | 0.25 | 6.1 |

Example 3

In contrast to substrates of the present invention experiments showed that in TR-FRET kinase reactions containing labeled poly-EY or poly-EAY co-polymers and a europium-labeled anti-phospho tyrosine antibody for the capture of the phosphorylated polymers, specific signal at 665 nm is very unstable over time. An assay comparing the stability of the random co-polymers poly-EAY, poly-EY and peptide BRB1 (SEQ ID No.3) is performed in 384-well format. Assay conditions are similar to those used in Example 1. The Eph4A tyrosine kinase is assayed at 2 nM with 50 nM of labeled peptide of SEQ ID No. 3, 200 nM labeled poly-EY or 200 nM poly-EAY and 50 micromolar ATP in 10 µL of kinase assay buffer. The reaction mixture is incubated for one hour at room temperature. Reactions are stopped with EDTA, and anti-phospho-tyrosine antibodies (clone PT66) labeled with the TR-FRET europium chelate donor dye are added to a concentration of 2 nM in a final volume of 20 µL. The TR-FRET signal emitted at 665 nm is read one, two, four, 18 and 24 hours after the addition of antibodies using a TR-FRET plate reader. Data obtained are shown in Table III and FIG. 2.

TABLE III

| Substrate | Incubation | Average Signal at 665 nm | % Decrease |
|---|---|---|---|
| BRB1 | 1 h | 134156 | |
| | 18 h | 117226 | 12.6% |
| | 24 h | 115534 | 13.9% |
| poly-EY | 1 h | 89035 | |
| | 18 h | 34987 | 60.7% |
| | 24 h | 30147 | 66.1% |
| poly-EAY | 1 h | 110300 | |
| | 18 h | 51379 | 53.4% |
| | 24 h | 45768 | 58.5% |

Figure 2:
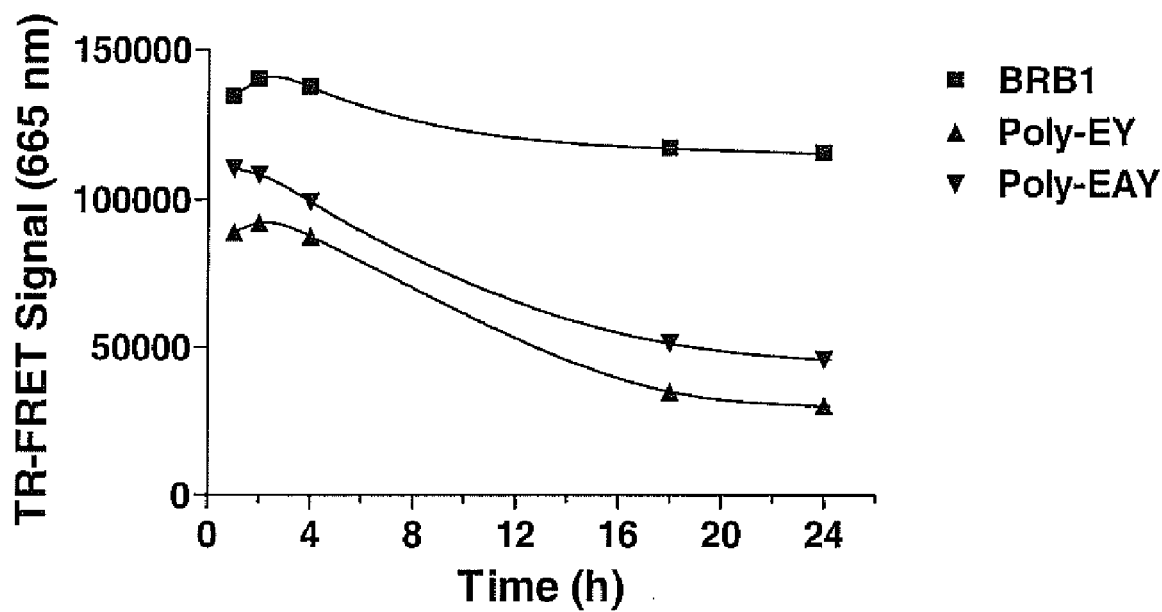
FIG. 2 is a graph illustrating stability of signal in TR-FRET assays using substrate peptides according to embodiments described herein compared with the stability of signal with the copolymers poly-EY and poly-EAY.

FIG. 2 shows the difference in signal stability between the labeled co-polymers poly-EY and poly-EAY and the labeled peptide of SEQ ID No. 3. Signal in TR-FRET kinase reactions using the substrate peptide of SEQ ID No. 3 is observed to be more stable several hours after the addition of the anti-phospho-capture antibody compared to poly EY and poly-EAY substrate. Indeed, after 24 h, the TR-FRET signal obtained using the substrate peptide of SEQ ID No. 3 was reduced by only 14%, while signal obtained using poly-EY and poly-EAY decreased by 66% and 59%, respectively.

Example 4

The tyrosine kinase substrate peptide AYE AYE AYE AYA EYE (SEQ ID NO.2) is modified by addition of an N-terminal cysteine, three spacer amino acids adjacent the cysteine (GGE) and by addition of two C-terminal basic amino acids (RR) to increase solubility at low pH, adjacent to a spacer amino acid (A). The resulting tyrosine kinase substrate peptide termed BRB2: CGG E AYE AYE AYE AYA EYE ARR (SEQ ID NO.4) is generated using well-known methods of peptide chemical synthesis. The tyrosine kinase substrate peptide of SEQ ID No. 4 contains five tyrosines, three of which are in the same module context (AYE) while other others are in a unique module context (AYA and EYE).

The BRB2 peptide is tested with 83 tyrosine kinases in assay conditions identical to those used for BRB1 in Example 1. Data obtained with BRB2 indicate that the peptide is phosphorylated by 65 kinases out of 83 (78%), with signal to noise ratio of >3.

Any patents or publications mentioned in this specification are incorporated herein by reference to the same extent as if each individual publication is specifically and individually indicated to be incorporated by reference. U.S. Patent Application Ser. No. 61/074,969, filed Jun. 23, 2008, is incorporated herein by reference in its entirety.

The compositions, methods and kits described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An isolated tyrosine kinase substrate peptide, comprising:
an amino acid sequence selected from the group consisting of: AYE AYE AYE K EYA EYA EYA K AYA EYE (SEQ ID NO. 1); AYE AYE AYE AYA EYE (SEQ ID NO.2); C AYE AYE AYE K EYA EYA EYA K AYA EYE R (SEQ ID NO. 3); CGG E AYE AYE AYE AYA EYE ARR (SEQ ID NO.4); and AYE AYE AYE B EYA EYA EYA B AYA EYE (SEQ ID NO. 5), where each B is a basic amino acid residue independently selected from histidine, lysine and arginine.

2. The tyrosine kinase substrate peptide of claim 1, wherein the peptide comprises at least one basic amino acid residue.

3. The tyrosine kinase substrate peptide of claim 2, the at least one basic amino acid residue is selected from the group consisting of: histidine, lysine and arginine.

4. The tyrosine kinase substrate peptide of claim 1, wherein the peptide has a net positive charge.

5. The tyrosine kinase substrate peptide of claim 1, wherein the peptide comprises a detectable label.

6. The tyrosine kinase substrate peptide of claim 1, wherein the detectable label is a FRET acceptor.

7. A plurality of tyrosine kinase substrate peptides, each peptide of the plurality comprising:
an amino acid sequence selected from the group consisting of: AYE AYE AYE K EYA EYA EYA K AYA EYE (SEQ ID NO. 1); AYE AYE AYE AYA EYE (SEQ ID NO.2); C AYE AYE AYE K EYA EYA EYA K AYA EYE R (SEQ ID NO. 3); CGG E AYE AYE AYE AYA EYE ARR (SEQ ID NO.4) and AYE AYE AYE B EYA EYA EYA B AYA EYE (SEQ ID NO. 5), where each B is a basic amino acid residue independently selected from histidine, lysine and arginine.

8. The plurality of tyrosine kinase substrate peptides of claim 7, wherein each peptide has a net positive charge.

9. A kit for detection of tyrosine kinase activity, comprising:
a tyrosine kinase substrate peptide wherein the tyrosine kinase substrate peptide comprises an amino acid sequence selected from the group consisting of: AYE AYE AYE K EYA EYA EYA K AYA EYE (SEQ ID NO. 1); AYE AYE AYE AYA EYE (SEQ ID NO.2); C AYE AYE AYE K EYA EYA EYA K AYA EYE R (SEQ ID NO. 3); CGG E AYE AYE AYE AYA EYE ARR (SEQ ID NO.4) and AYE AYE AYE B EYA EYA EYA B AYA EYE (SEQ ID NO. 5), where each B is a basic amino acid residue independently selected from histidine, lysine and arginine.

10. The kit for detection of tyrosine kinase activity of claim 9, wherein the peptide comprises a detectable label.

11. The kit for detection of tyrosine kinase activity of claim 10, wherein the detectable label is a FRET acceptor.

12. The kit for detection of tyrosine kinase activity of claim 10, wherein the N-terminus of the peptide comprises the detectable label.

13. The kit for detection of tyrosine kinase activity of claim 9, wherein the peptide comprises at least one basic amino acid residue.

14. The kit for detection of tyrosine kinase activity of claim 13, the at least one basic amino acid residue is selected from the group consisting of: histidine, lysine and arginine.

15. The kit for detection of tyrosine kinase activity of claim 9, wherein the peptide has a net positive charge.

* * * * *